US012710340B2

(12) United States Patent
Vincent et al.

(10) Patent No.: US 12,710,340 B2
(45) Date of Patent: Aug. 18, 2026

(54) PASSIVE DIFFUSION BAG SAMPLERS WITH IMPROVED PERFORMANCE

(71) Applicant: Aeris Scientific, LLC, Longview, WA (US)

(72) Inventors: Stephen W. Vincent, Longview, WA (US); Douglas W. Later, Sandy, UT (US); Evan A. Reese, Nashville, TN (US); Jordan K. Harrison, Lebanon, TN (US)

(73) Assignee: Aeris Scientific, LLC, Longview, WA (US)

( * ) Notice: Subject to any disclaimer, the term of this patent is extended or adjusted under 35 U.S.C. 154(b) by 247 days.

(21) Appl. No.: 18/334,600

(22) Filed: Jun. 14, 2023

(65) Prior Publication Data

US 2024/0418609 A1 Dec. 19, 2024

(51) Int. Cl.
*G01N 1/40* (2006.01)
*G01N 1/14* (2006.01)
(Continued)

(52) U.S. Cl.
CPC ............. *G01N 1/14* (2013.01); *G01N 1/4005* (2013.01); *G01N 33/1826* (2013.01); *E21B 49/081* (2013.01); *G01N 2001/1472* (2013.01)

(58) Field of Classification Search
CPC .... G01N 1/14; G01N 1/4005; G01N 33/1826; G01N 2001/1472; G01N 1/2294; G01N 2001/149; G01N 1/16; G01N 1/2202; G01N 1/2205; E21B 49/081
USPC ........... 73/19.1, 19.12, 61.59, 64.56, 863.21, 73/863.23, 864.31, 864.51, 864.73, 73/864.74
See application file for complete search history.

(56) References Cited

U.S. PATENT DOCUMENTS

| | | | | |
|---|---|---|---|---|
| 7,430,929 B1 * | 10/2008 | Vroblesky | ................. | E02D 1/06 73/864.74 |
| 2012/0297900 A1 * | 11/2012 | Intelisano | ................ | G01N 1/10 73/863.23 |
| 2014/0290391 A1 * | 10/2014 | Varhol | ..................... | G01N 1/10 73/863.23 |

FOREIGN PATENT DOCUMENTS

| | | | | |
|---|---|---|---|---|
| JP | 2021156881 A * | 10/2021 | ............... | G01N 1/14 |

OTHER PUBLICATIONS

Don A. Vroblesky, User's Guide for Polyethylene-Based Passive Diffusion Bag Samplers to Obtain Volatile Organic Compound Concentrations in Wells, U.S. Geological Survey Water-Resources Investigations Report 01-4060, South Carolina, 2001, pp. 1-67.

(Continued)

*Primary Examiner* — Robert R Raevis
(74) *Attorney, Agent, or Firm* — Morriss O'Bryant; Compagni Cannon, PLLC

(57) ABSTRACT

The present invention is a system and method for providing a passive diffusion bag sampler that is suitable for obtaining concentrations of a variety of volatile organic compounds, wherein the passive diffusion bag sampler includes an outer protective rigid mesh tube, an inner polyethylene bag disposed inside the outer protective rigid mesh tube, a ring coupled to and disposed at either end of the outer protective rigid mesh tube, a cap also disposed at either end of the outer protective rigid mesh tube and inside the ring but over the inner polyethylene bag and forming a watertight seal, and a non-removable plug disposed in an aperture through each of the caps, wherein the passive diffusion bag sampler may be held and poured using a single hand because of the rigidity of the passive diffusion bag sampler.

20 Claims, 9 Drawing Sheets

(51) Int. Cl.
*G01N 33/18* (2006.01)
*E21B 49/08* (2006.01)

(56) References Cited

OTHER PUBLICATIONS

Burgess, R. M., S. B. Kane Driscoll, A. Burton, P. M. Gschwend, U. Ghosh, D. Reible, S. Ahn, T. Thompson. Laboratory, Field, and Analytical Procedures for Using Passive Sampling in the Evaluation of Contaminated Sediments: User's Manual. U.S. Environmental Protection Agency, Washington, DC, EPA/600/R-16/357, Feb. 2017, pp. 1-167.

* cited by examiner

PASSIVE DIFFUSION BAG SAMPLERS WITH IMPROVED PERFORMANCE

BACKGROUND

Field of the Invention: This invention relates generally to passive diffusion bag (PDB) samplers that are suitable for obtaining concentrations of a variety of volatile organic compounds (VOCs).

Description of Related Art: The prior art for passive diffusion bag samplers may be described as PDB samplers that are used to obtain concentrations of a variety of volatile organic compounds in ground water at monitoring wells. The suggested application of the method is for long-term monitoring of VOCs in ground-water wells.

The effectiveness of the use of a PDB sampler is dependent on the ability to deploy the PDB sampler in a horizontal flow of water through a well screen, and that the quality of the water is representative of the ground water in the aquifer directly adjacent to a screen.

FIG. 1A shows a profile view of a typical prior art PDB sampler 10 consisting of a low-density polyethylene (LDPE) lay-flat tube that is closed at a top end 12 and at a bottom end 14 and is pre-filled with deionized or some sort of purified water.

FIG. 1B is a profile view of a typical prior art mesh bag 16 that is used to cover the PDB sampler 10 of FIG. 1A. The mesh bag 16 holds the PDB sampler 10 suspended inside it, with water passing through the mesh bag and into the PDB sampler. The PDB sampler 10 is positioned at a target location within the water to be sampled by attachment to a weighted line. The PDB samplers 10 are left in place long enough for the well water, contaminant distribution, and flow dynamics to restabilize following PDB sampler deployment in the water source.

The prior art PDB sampler 10 has several drawbacks that make use of the existing design a problem.

A first problem of the prior art PDB sampler 10 is the nature of the low-density polyethylene (LDPE) lay-flat tube shown in FIG. 1A. The polyethylene (LDPE) lay-flat tube is a non-rigid material meaning that without an external or internal structure to provide support or an internal pressure to provide a supporting force, the polyethylene material is flexible to the point that it will not remain straight when held horizontally. In other words, the polyethylene (LDPE) lay-flat tube will respond like a non-rigid plastic material and hang in a limp or floppy manner.

It is noted that the polyethylene material is shown being formed into a lay-flat tube. The tube-like structure of the PDB sampler 10 provides insufficient support, given the nature of the polyethylene material, to remain upright in a vertical orientation if only held along a bottom edge.

The problem with the PDB sampler 10 being a non-rigid structure is demonstrated when in use. In operation, the PDB sampler 10 is filled with purified water. When the water is inserted, the PDB sampler 10 may or may not have enough internal pressure from the water to remain rigid. However, once the PDB sampler 10 is unsealed to extract the water containing the VOCs, the PDB sampler is immediately flexible enough to collapse and spill the sample inside if not handled carefully.

A user must still extract the water from the PDB sampler 10 after it has had time to allow VOCs to be sampled. The user needs to open the PDB sampler 10 at or near the top end 12. This is done in one of two ways. The first way is for the user to cut off the top end 12 of the PDB sampler 10. The second way is to pierce the side of the PDB sampler 10 with a rigid straw. In both methods, the user must then pour the contents of the PDB sampler 10 into multiple VOC sample vials for transport and laboratory testing of the VOC components.

If the top end 12 or the side of the PDB sampler 10 is pierced with a straw, the user must use two hands to control the PDB sampler 10 in order to tip the PDB sampler 10 forward and pour out the sample.

If the top end 12 of the PDB sampler 10 is cut off, then the user must hold the PDB sampler near the top end and the bottom end 14 in order to pour out the sample while trying to lose only a small portion of the sample and fill as many sample vials as possible.

The disadvantage of both of these methods of pouring out the sample from the PDB sampler 10 is that it is a two-handed operation because the PDB sampler 10 is non-rigid and must be poured using two hands. The user must use one hand to direct the sample into the vials, and the other hand to lift the bottom of the PDB sampler 10 to allow it to pour.

Another disadvantage of the two-handed pouring operation of the PDB sampler 10 is that the PDB sampler is typically used to fill multiple sample vials. The user risks knocking over the multiple vials while trying to fill them because there is no free hand to hold the sample vials or to put on a cap when each vial is filled. Thus, the process of pouring out the samples typically requires two people when using a PDB sampler 10 of the prior art.

Another disadvantage of the PDB sampler 10 of the prior art has to do with turbulent flow when pouring the sample. It is important that turbulent flow of the water containing the VOCs be avoided in order to avoid the release of VOCs and thereby resulting in the potential loss of VOCs and an inaccurate measurement of the sample. Unfortunately, both methods of pouring the sample from the PDB sampler 10 may easily result in turbulent water flow.

A final disadvantage that should be mentioned is that the prior art susceptibility to mishandling may easily lead to contamination of the samples from handling by the sampler and the surrounding environment.

For example, when the top end 12 is cut off the PDB sampler 10, water is pouring over a limp edge of polyethylene. The straw is likely to be difficult to direct into a vial and it is likely leaking where it has pierced the side of the PDB sampler 10 and may be dripping into the stream of water flowing from the straw.

Another disadvantage of the PDB sampler 10 is the mesh bag 16. If the mesh bag is placed over the PDB sampler 10 and lowered into a well, the mesh bag is also not a rigid structure but is instead a limp and flexible mesh material that may easily catch on any protrusions in a well where the sample is being taken. Furthermore, the mesh bag 16 may rip or tear, thereby allowing the PDB sampler 10 inside to be damaged and possibly leak. The mesh bag 16 may also fray and allow loose strings of mesh material to dangle in the well, allowing the mesh material to catch on protrusions and thus making it difficult to extract the PDB sampler 10 from the well. Thus, the mesh bag 16 fails to offer any protection to the PDB sampler 10.

The PDB sampler 10 also lacks refinement in providing a system for linking multiple PDB samplers 10 in a linked chain. It is often the case that multiple PDB samplers 10 need to be sequentially linked together in series so that samples may be taken at multiples depths within a water source.

As shown in FIG. 1A, the prior art PDB sampler 10 may include a hole 20 at the top end 12 and at the bottom end 14.

FIG. 2 is a profile view of a plurality of PDB samplers 10 coupled together to form a chain. At the bottom of the chain of PDB samplers 10 a weight 22 may be attached so that the PDB samplers 10 are able to reach a desired depth within the water source. Each of the PDB samplers 10 is coupled to each other and to the weight 22 by a zip tie 24. The dots 26 are used to indicate that there may be any number of the PDB samplers 10 coupled together to form a desired chain length. The use of zip ties 24 may be cumbersome and clumsy as they each must be tightened to a desired amount.

Accordingly, it would be an advantage over the prior art to provide a PDB sampler that may be held and poured using a single hand, and thereby allowing the user to hold the sample vials with the free hand. It would be another advantage to provide a PDB sampler that was protected by a surrounding holder. It would be another advantage to provide a more refined method of attaching a plurality of PDB samplers in a chain that was not awkward and provided a uniform linkage length. Finally, it would be an advantage to provide a system for providing consistent non-turbulent flow of the sample into the sample vials.

BRIEF SUMMARY

The present invention is a system and method for providing a passive diffusion bag sampler that is suitable for obtaining concentrations of a variety of volatile organic compounds, wherein the passive diffusion bag sampler includes an outer protective rigid mesh tube, an inner polyethylene bag disposed inside the outer protective rigid mesh tube, a ring coupled to and disposed at either end of the outer protective rigid mesh tube, a cap also disposed at either end of the outer protective rigid mesh tube and inside the ring but over the inner polyethylene bag and forming a watertight seal, and a plug disposed in an aperture through each of the caps, wherein the passive diffusion bag sampler may be held and poured using a single hand because of the rigidity of the passive diffusion bag sampler.

While the embodiments below are described as using a polyethylene bag, it is noted that any bag that is capable of performing the function of the polyethylene bag may be substituted into the embodiments without changing the scope of the claims.

In a first aspect of the invention, the outer protective mesh tube is a rigid material that will not bend to a point of folding when filled with water and held horizontally.

In a second aspect of the invention, the inner polyethylene bag may also be a rigid material.

In a third aspect of the invention, the outer protective rigid mesh tube, and the inner polyethylene bag both have a circular cross-sectional shape and form cylinders.

In a fourth aspect of the invention, the ring and the cap provide mechanical structure between the outer protective rigid mesh tube and the inner polyethylene sample collection bag.

In a fifth aspect of the invention, the cap includes an aperture that provides non-turbulent flow of water from the passive diffusion bag sampler.

These and other embodiments of the present invention will become apparent to those skilled in the art from a consideration of the following detailed description taken in combination with the accompanying drawings.

DETAILED DESCRIPTION

Reference will now be made to the drawings in which the various embodiments of the present invention will be discussed so as to enable one skilled in the art to make and use the invention. It is to be understood that the following description illustrates embodiments of the present invention and should not be viewed as narrowing the claims which follow.

Figures 1A, 1B:
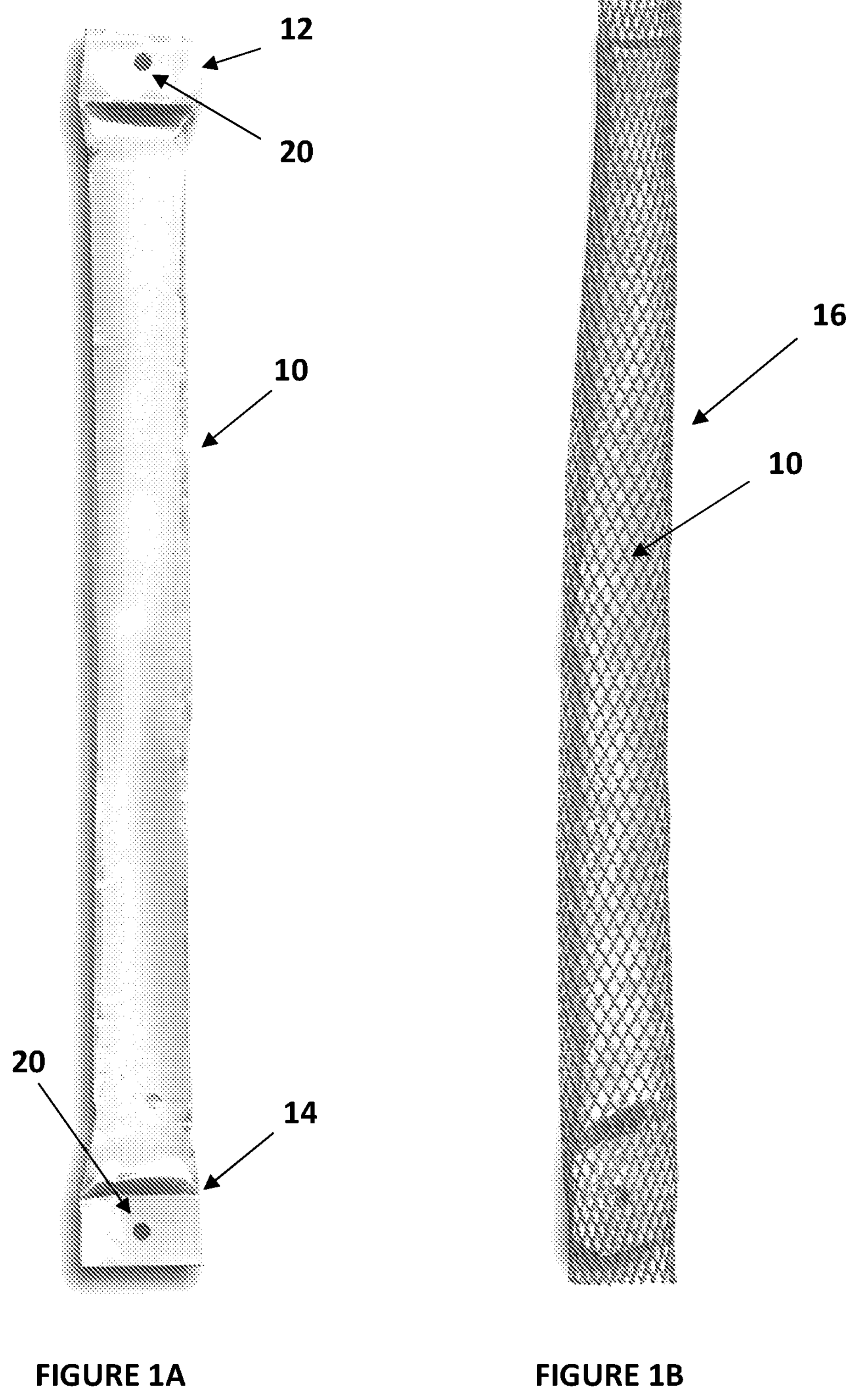
FIG. 1A is a profile view of a PDB sampler in the prior art.
FIG. 1B is a profile view of a PDB sampler disposed within a mesh bag in the prior art.
Figure 2:
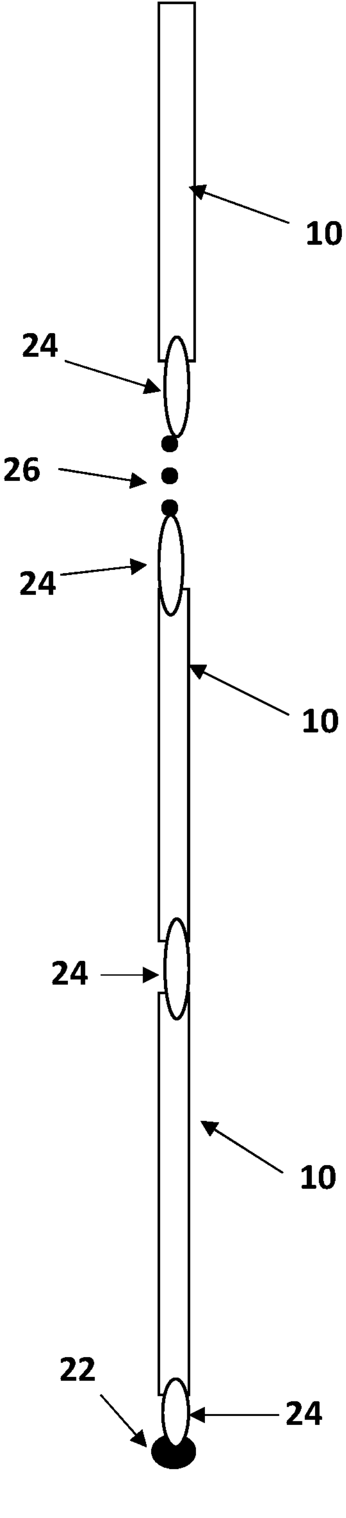
FIG. 2 is an illustration showing a chain of PDB samplers connected together.
Figure 3:
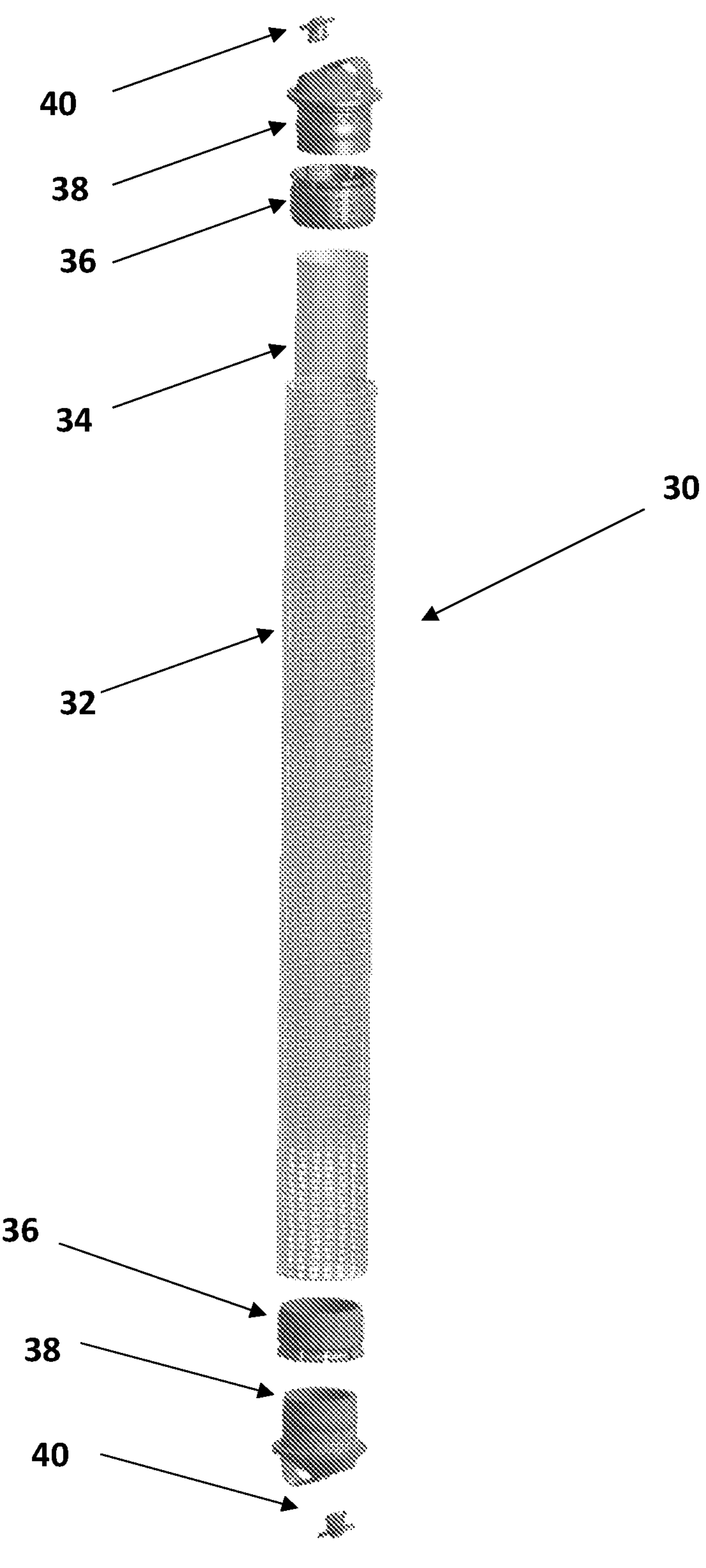
FIG. 3 is a perspective and exploded view of the components of the first embodiment of the invention.

FIG. 3 is a perspective view of the components of a PDB sampler 30 of a first embodiment of the invention. This figure also shows key features of the first embodiment which differentiate it from the prior art.

The PDB sampler 30 may include an outer protective rigid mesh tube 32, an inner polyethylene bag 34, a ring 36, a cap 38, and a plug 40.

Figure 4:
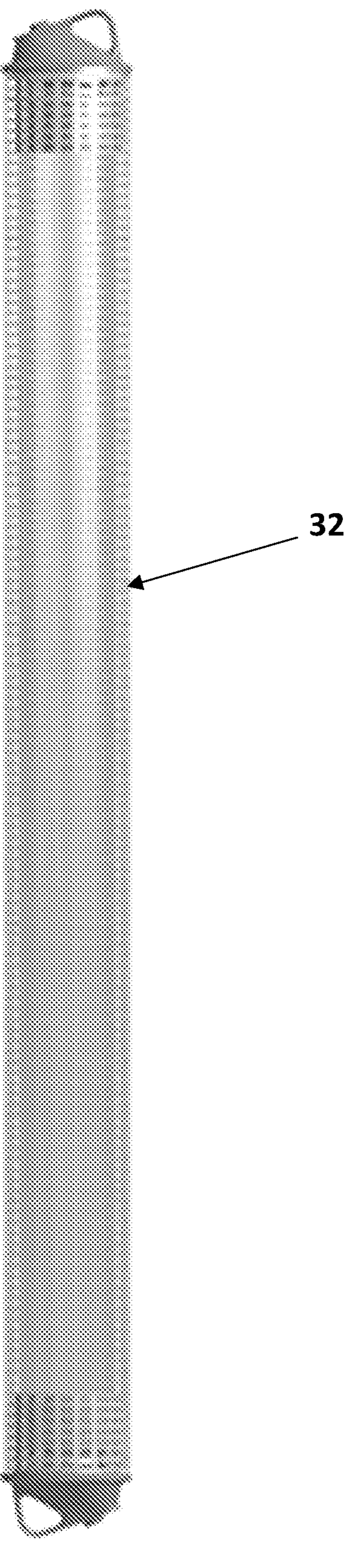
FIG. 4 is a profile view of the assembled components of the first embodiment of the invention.

As shown in FIG. 4, the outer protective rigid mesh tube 32 is made of a rigid plastic or plastic-like material that allows water to diffuse to the inner polyethylene bag 34. Unlike the mesh bag 16 of the prior art, the outer protective rigid mesh tube 32 retains a cylindrical shape at all times. The outer protective rigid mesh tube 32 is sufficiently rigid such that when the inner polyethylene bag 34 is empty or filled with water, the outer protective rigid mesh tube remains straight and rigid.

A particular advantage of the outer protective rigid mesh tube 32 is that the user may hold it in the middle and pour the sample from the PDB sampler 30 with one hand. Because the outer protective rigid mesh tube 32 does not substantially flex and bend to a point of folding, the user may easily pour the sample into sample vials, holding the outer protective rigid mesh tube in one hand and a sample vial in the other.

Therefore, while the outer protective rigid mesh tube 32 may slightly bend, it may not bend to the point that it will fold, crimp or crease. In other words, the inner polyethylene bag 34 may hold enough water to cause the prior art bags to easily flop or fold over making one-handed pouring an impossibility. In contrast, while the outer protective rigid mesh tube 32 may show a slight curvature when held horizontally, it will have sufficient rigidity and strength to resist folding over and creasing. Therefore, while a slight bend is permitted without detriment to the function of the outer protective rigid mesh tube 32, folding over and forming a crease in the outer protective rigid mesh tube is not.

While the first embodiment shows that the outer protective rigid mesh tube 32 is cylindrical in shape, it is noted that the cylindrical shape does not need to have a circular cross-section but may be any multi-sided polygonal shape and include flat surfaces, flat surfaces and curved surfaces, or just curved surfaces. For example, the cross-section of the cylinder could be a non-circular ellipse or have multi-sided flat surfaces and form a triangle, a square, a rectangle, a pentagon, an octagon, etc.

What is important in the first embodiment is that whatever the cross-sectional shape of the cylinder, the outer protective rigid mesh tube 32 may not bend to the point of folding and creasing when pouring the sample.

Another feature of the outer protective rigid mesh tube 32 is that it is not made out of loose fibers and therefore it will not fray if it brushes against sharp edges in a casing of the monitoring well water source. Because it is a rigid material, it will also resist bending to the point of folding inwards, and thereby protect the inner polyethylene bag 34 from punctures and abrasions.

The outer protective rigid mesh tube 32 is disposed around the inner polyethylene bag 34. The inner polyethylene bag 34 only has to fit within the outer protective rigid mesh tube 32 and may loosely or tightly fit within. By leaving a small gap between the outer protective rigid mesh tube 32 and the inner polyethylene bag 34, more surface area of the inner polyethylene bag 34 may be exposed to the water source and therefore may allow the VOCs to diffuse into the purified water more readily inside the inner polyethylene bag.

The inner polyethylene bag 34 may be comprised of polyethylene or any other appropriate material that will allow the diffusion of VOCs just as the prior art. However, unlike the prior art, the inner polyethylene bag 34 may retain a cross-sectional shape even when it is not filled with water. In other words, the inner polyethylene bag 34 is not a lay-flat tube as taught in the prior art, but instead it may have a cross-sectional shape that it keeps whether it is full or empty of purified water.

The cross-section shape of the inner polyethylene bag 34 may also be any of the cross-sectional shapes of the outer protective rigid mesh tube 32. In the first embodiment of the invention, the inner polyethylene bag 34 is also a cylindrical shape with a circular cross-section.

Figure 5A:
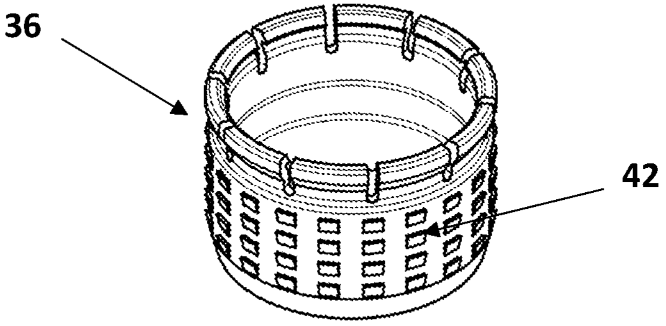
FIG. 5A is a perspective view of the ring.
Figure 5B:
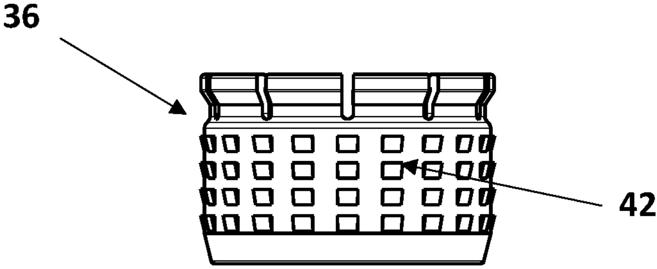
FIG. 5B is a profile view of the ring.

As shown in FIG. 3, each end of the outer protective rigid mesh tube 32 has disposed thereon a ring 36 as shown in a close-up view in FIGS. 5A and 5B. The ring 36 is coupled to the outer protective rigid mesh tube 32 using any appropriate method that prevents removal of the ring from the ends of the outer protective rigid mesh tube. The ring 36 may be disposed inside and flush with the ends of the outer protective rigid mesh tube 32. In the first embodiment shown in FIGS. 5A and 5B, the ring 36 is shown having a plurality of projections 42 around the outer circumference of the ring. These projections 42 will grip the inner surface of the outer protective rigid mesh tube 32 and securely hold it in place. The ring 36 may also function to strengthen the rigidity of the outer protective rigid mesh tube 32 by not allowing the ends to inwardly collapse. The ring 36 may be manufactured of any rigid material and may be made of a rigid plastic or plastic-like material.

The cross-sectional shape of the ring 36 may match the cross-sectional shape of the outer protective rigid mesh tube 32 so that they are securely connected.

Figure 6A:
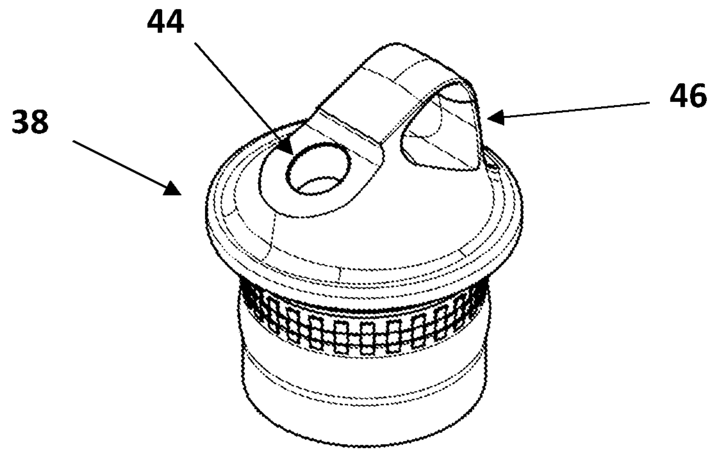
FIG. 6A is a perspective view of the cap.
Figure 6B:
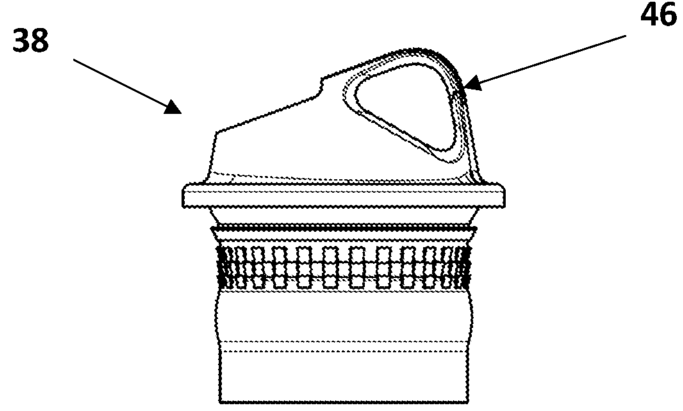
FIG. 6B is a profile view of the cap.

At each end of the PDB sampler 30 is disposed the cap 38 which is shown in close-up detail in FIGS. 6A and 6B. The cross-sectional shape of the cap 38 may match the cross-sectional shape of the ring 36 so that they are securely connected. The cap 38 may be slightly smaller in cross-section shape than the ring 36 such that they form a connection. In the first embodiment, the connection may be a snap connection that may not be undone, or even a friction fit connection. What is important is that when the cap 38 is inserted into the ring 36, it is a tight connection such that the cap will not pull out of the ring without substantial effort or destruction of the components. Thus, the weight of a plurality of PDB samplers 30 linked together in a chain will not be sufficient to pull the cap 38 from the ring 36. However, the user may be able to pry the cap 38 loose from the ring 36.

It is important that when the cap 38 is inserted into the ring 36 that the cap forms a water-tight seal over both ends of the inner polyethylene bag 34. In other words, the cap 38 is disposed inside the ring 36 but around the outside of the inner polyethylene bag 34. The cap 38 is of sufficient length that all of the portions of the cap that are disposed within the outer protective rigid mesh tube 32 are also disposed over the ends of the inner polyethylene bag 34. The water-tight seal of the cap 38 over the inner polyethylene bag 34 ensures that the purified water inside the inner polyethylene bag is not contaminated by anything other than VOCs diffusing through the inner polyethylene bag.

Just as with the cross-sectional shape of the outer protective rigid mesh tube 32, the inner polyethylene bag 34, and the ring 36, the cap 38 may also have the same cross-sectional shapes. The cap may also be manufactured out of the same materials as the ring 36. The material selected is most likely plastic or other rigid plastic-like material.

In the first embodiment of the cap 38, the cap may include a feature that enables the PDB sampler 30 to be linked in a chain of a plurality of PDB samplers. Accordingly, the first embodiment may include an attachment loop 46 having any desired shape that allows an object to be attached to it for connecting to another PDB sampler 30, to a weight, or to a line or string. The shape of the attachment loop 46 may be any closed loop or open loop shape with any desired cross-section that will enable another object to be coupled to the attachment loop.

Figure 6C:
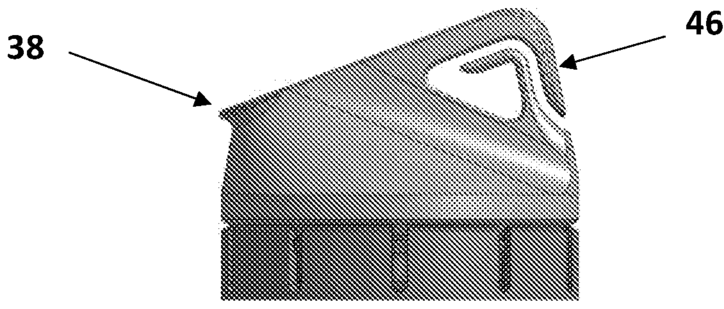
FIG. 6C is a profile view of an alternative embodiment of the cap.

FIG. 6C is provided as an alternative embodiment of the cap 38 used in the PDB sampler 30. In this alternative embodiment, the shape of the attachment loop 46 is shown as having an open loop shape with any desired cross-section that will enable another object to be coupled to the attachment loop.

The chain of the plurality of PDB samplers may be a sequential series of PDB samplers connected from one to another. Alternatively, the PDB samplers may all be attached to a single line at various points along a length of the line. It is also noted that while single-use zip ties were used in the prior art, they may still be used with the embodiments of the invention.

While the prior art uses single-use zip ties to connect PDB samplers in series, the first embodiment of the present invention may have a coupling device that may be reused. For example, the first embodiment may use a carabiner or carabiner-like device to connect PDB samplers in series. Generically, the carabiner may be described as a coupling link with a safety closure.

A final feature of the cap 38 is an aperture 44 disposed through the cap. The aperture 44 extends all the way through the cap 38 and enables water inside the inner polyethylene bag 34 to be poured out of the PDB sampler 30 and into a sample vial.

Most importantly, the shape of the aperture 44 may enable the water to be poured in a non-turbulent manner from the inner polyethylene bag 34, thereby preventing the loss of VOCs from the sample in the PDB sampler 30. Thus, the shape of aperture 44 is such that it produces a non-turbulent flow of water. Advantageously, no straw needs to be inserted into the inner polyethylene bag 34, nor does the inner polyethylene bag need to be cut as in the prior art.

Figure 7A:
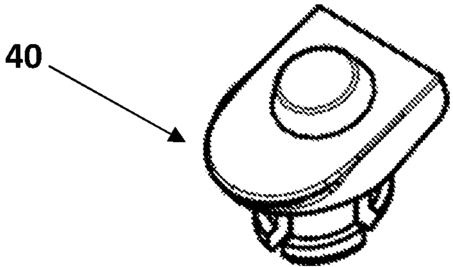
FIG. 7A is a perspective view of the plug.
Figure 7B:
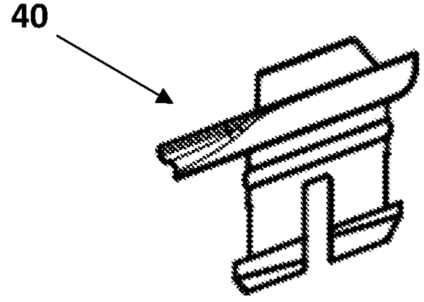
FIG. 7B is a profile view of the plug.

The aperture 44 is normally sealed until the water sample is ready to be poured from the inner polyethylene bag 34. As shown in FIGS. 7A and 7B, the plug 40 is inserted into the apertures 44 at each end of the PDB sampler 30 to seal them until ready to pour.

An important aspect of the embodiments is that the cap 38 may or may not be reusable. In the first embodiment of the invention, the plug 40 is made so that it is not removable, making the plug and the cap 38 non-reusable, or a single-use device. In other words, if the plug 40 is not removable from the aperture 44 then it may be cut or sheared off to access the VOC sample within the inner polyethylene bag 34. The plug 40 may be manufactured of any material that may form a water-tight seal in the aperture 44. For example, the plug may be inert plastic, rubber, plastic-like, or a rubber-like material.

It should therefore be understood that the embodiments of the invention may be directed to what is disposable and what is reusable in the PDB sampler 30. In the first embodiment, the PDB sampler 30 is entirely disposable. In an alternative embodiment, the inner polyethylene bag 34, the cap 38 and the plug 40 may be disposable. Accordingly, some components of the PDB sampler 30 may be disposable, single-use items, and others may be reusable. However, in the first embodiment, the entire PDB sampler 30 is disposable in order to protect the integrity of the VOCs being sampled using the inner polyethylene bag 34.

In an alternative embodiment, the plug 40 may be made so that it may be removed from the aperture 44 and also reinserted to make a water-tight seal. The plug 40 may be manufactured of any material that may form a water-tight seal in the aperture 44. For example, the plug may be inert plastic, rubber, plastic-like, or a rubber-like material.

Figure 8:
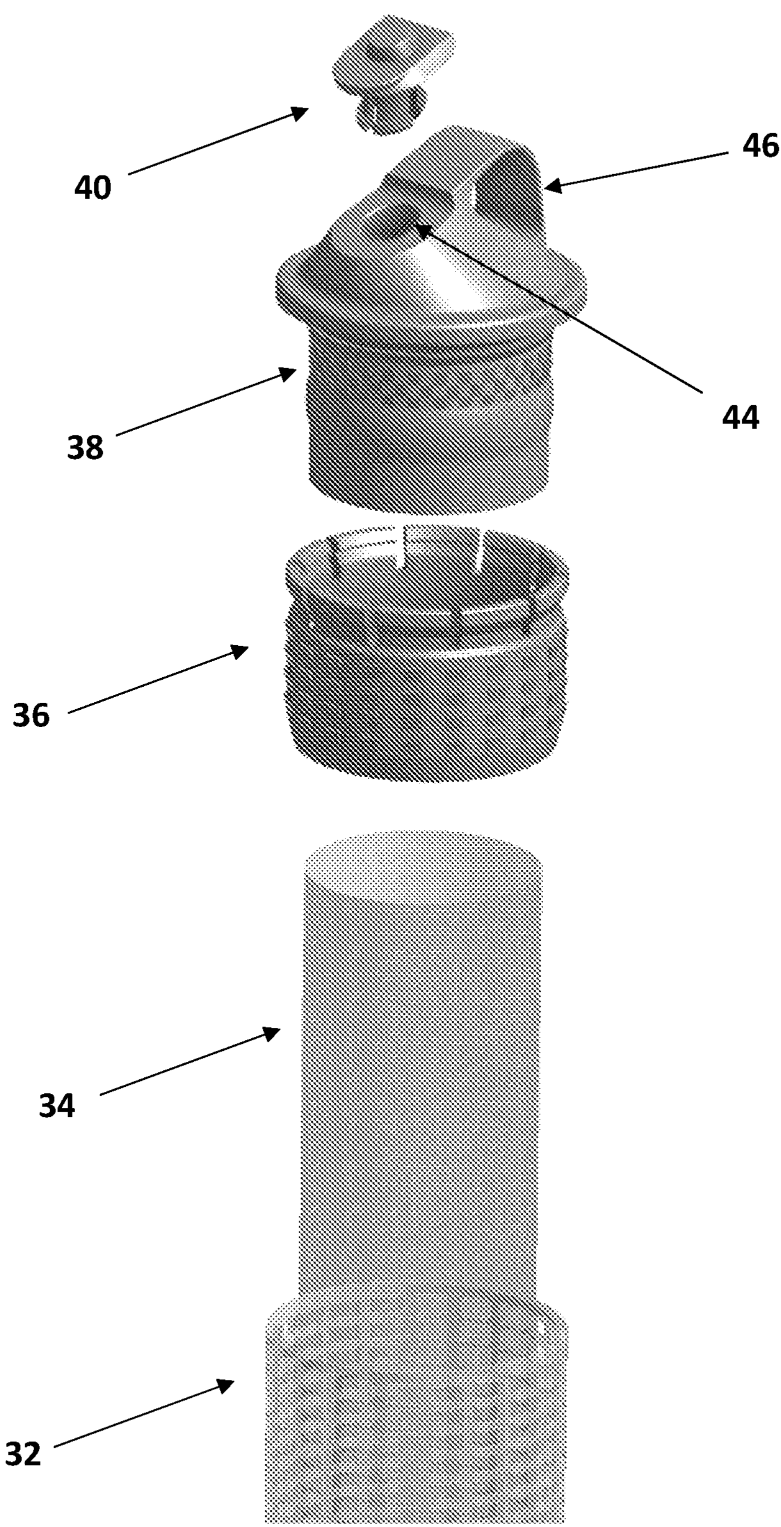
FIG. 8 is a perspective and exploded view of the components at one end of the PDB sampler of the first embodiment of the invention.

FIG. 8 is provided as a close-up perspective and exploded view of the components at one end of the first embodiment of the PDB sampler 30. The components are duplicated at the opposite end of the PDB sampler 30. The PDB sampler 30 includes the outer protective rigid mesh tube 32, the inner polyethylene bag 34, the ring 36, the cap 38, and the plug 40. The cap 38 may also include the ring 42, and the aperture 44.

Figure 9:
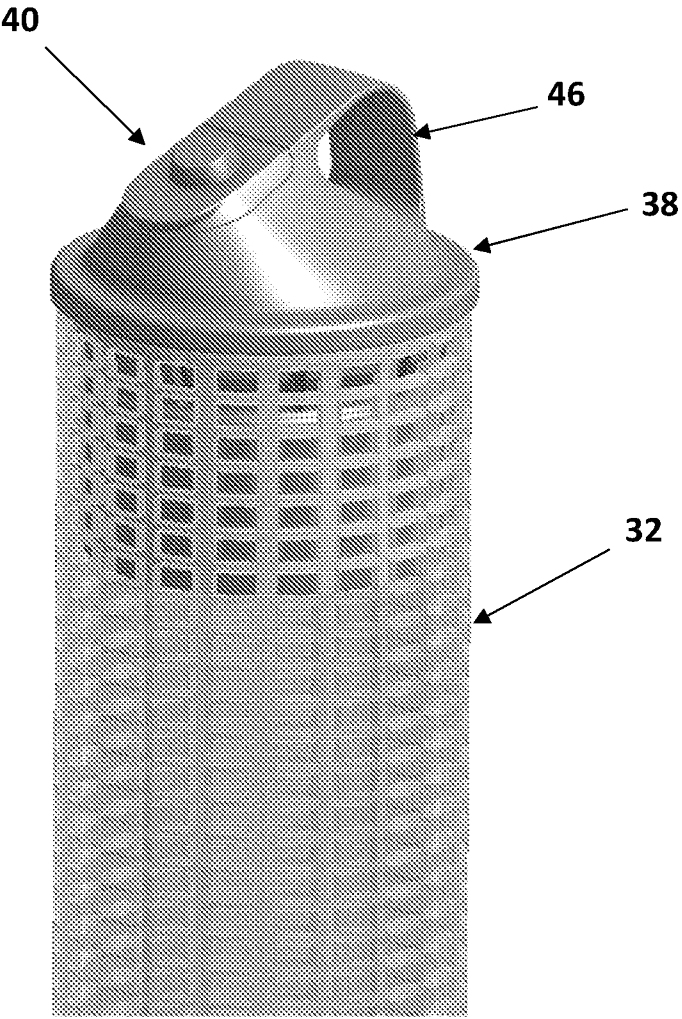
FIG. 9 is a profile view of the assembled components at one end of the PDB sampler of the first embodiment of the invention.

FIG. 9 is provided as a close-up perspective and assembled view of the components at one end of the first embodiment of the PDB sampler 30. This figure shows all of the components of FIG. 8 but coupled together in an assembled form that is ready for use.

In the first embodiment of the invention, the cross-sectional shape of the outer protective rigid mesh tube 32, the inner polyethylene bag 34, the ring 36, and the cap 38 may be circular.

The first embodiment of the PDB sampler is a non-reusable or disposable device. The inner polyethylene bag 34 may not be replaced or separated from the other components in the PDB sampler 30.

In another embodiment of the invention, the ring 36 and the cap 38 may be combined into a single cap unit. While not as easy to use as when the ring 36 and the cap 38 are separate components, it is noted that they may be combined to offer the same functionality.

In summary, the apparatus of the first embodiment of the invention is as follows. A passive diffusion bag sampler suitable for obtaining concentrations of a variety of volatile organic compounds, said passive diffusion bag sampler comprised of an outer protective rigid mesh tube, wherein the rigid mesh tube is cylindrical and sealed at each end, an inner polyethylene bag that is cylindrical and disposed within the rigid mesh tube, wherein the inner polyethylene bag is sealed at each end and allows the passage of volatile organic compounds to diffuse through a surface of the inner polyethylene bag, a ring disposed inside each end of the outer protective rigid mesh tube, wherein each ring is rigid and flush with an end of the outer protective rigid mesh tube, a cap disposed on each end of the outer protective rigid mesh tube to thereby seal the outer protective rigid mesh tube and the inner polyethylene bag, wherein each cap is also disposed inside the ring to form a tight connection, and wherein the cap is also disposed over each end of the inner polyethylene bag, an aperture disposed through each cap, wherein the aperture extends from outside the passive diffusion bag sampler to an interior of the inner polyethylene bag, and a plug disposed in the aperture of each cap.

Similarly, a summary of the method of use of the first embodiment is as follows. A method for obtaining concentrations of a variety of volatile organic compounds using a passive diffusion bag sampler, said method comprising providing an outer protective rigid mesh tube, wherein the rigid mesh tube is cylindrical and sealed at each end, an inner polyethylene bag that is cylindrical and disposed within the rigid mesh tube, wherein the inner polyethylene bag is sealed at each end and allows the passage of volatile organic compounds to diffuse through a surface of the inner polyethylene bag, a ring disposed inside each end of the outer protective rigid mesh tube, wherein each ring is rigid and flush with an end of the outer protective rigid mesh tube, a cap disposed on each end of the outer protective rigid mesh tube to thereby seal the outer protective rigid mesh tube and the inner polyethylene bag, wherein each cap is also disposed inside the ring to form a tight connection, and wherein the cap is also disposed over each end of the inner polyethylene bag, an aperture disposed through each cap, wherein the aperture extends from outside the passive diffusion bag sampler to an interior of the inner polyethylene bag, wherein the aperture is shaped so as to enable a non-turbulent flow of water from the passive diffusion bag sampler, and a plug disposed in the aperture of each cap, filling the inner polyethylene bag with purified water and sealing the inner polyethylene bag with the plug, disposing the passive diffusion bag sampler in the water sample, withdrawing the passive diffusion bag sampler after volatile organic compounds have been diffused into the inner polyethylene bag, cutting or otherwise shearing off one plug from one of the apertures in the passive diffusion bag sampler, and pouring the water from the passive diffusion bag sampler using a first hand and in a non-turbulent manner.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A passive diffusion bag sampler suitable for obtaining concentrations of a variety of volatile organic compounds, said passive diffusion bag sampler comprised of:

an outer protective rigid mesh tube, wherein the rigid mesh tube is cylindrical and sealed at each end;

an inner polyethylene bag that is cylindrical and disposed within the rigid mesh tube, wherein the inner polyethylene bag is sealed at each end and allows the passage of volatile organic compounds to diffuse through a surface of the inner polyethylene bag;

a ring disposed inside each end of the outer protective rigid mesh tube, wherein each ring is rigid and flush with an end of the outer protective rigid mesh tube;

a cap disposed on each end of the outer protective rigid mesh tube to thereby seal the outer protective rigid mesh tube and the inner polyethylene bag, wherein each cap is also inserted inside a corresponding one of the rings to form a tight connection and is disposed over a corresponding end region of the inner polyethylene bag so as to and is of sufficient length to overlie said end of the inner polyethylene bag such that insertion of the cap into the ring forms a water-tight seal over said end of the inner polyethylene bag;

an aperture disposed through each cap, wherein the aperture extends from outside the passive diffusion bag sampler to an interior of the inner polyethylene bag; and a plug disposed in the aperture of each cap.

2. The passive diffusion bag sampler as defined in claim 1 wherein the inner polyethylene bag is rigid.

3. The passive diffusion bag sampler as defined in claim 1 wherein the cross-sectional shape of the outer protective rigid mesh tube, the inner polyethylene bag, the ring, and the cap are all the same.

4. The passive diffusion bag sampler as defined in claim 3 wherein the cross-sectional shape is selected from the group of cross-sectional shapes comprised of a circle, a non-circular ellipse, a polygon, or a combination of an ellipse and a polygon.

5. The passive diffusion bag sampler as defined in claim 1 wherein each cap is further comprised of a closed attachment loop.

6. The passive diffusion bag sampler as defined in claim 5 wherein the passive diffusion bag sampler is further comprised of:

a first passive diffusion bag sampler as defined in claim 1 having a first attachment loop;

a second passive diffusion bag sampler as defined in claim 1 having a second attachment loop; and a coupling link with a safety closure coupled to the first attachment loop and to the second attachment loop such that the first and second diffusion bag samplers are linearly coupled.

7. The passive diffusion bag sampler as defined in claim 1 wherein each cap is further comprised of an open attachment loop.

8. The passive diffusion bag sampler as defined in claim 1 wherein the inner polyethylene bag and the cap on each end form a water-tight seal wherein each cap is inserted inside a corresponding ring to form a tight connection and is disposed inside the ring but around the outside of a corresponding end of the inner polyethylene bag and is of sufficient length to overlie said end such that insertion of the cap into the ring forms the water-tight seal over the end of the inner polyethylene bag so that the volatile organic compounds may only diffuse through the surface of the inner polyethylene bag.

9. The passive diffusion bag sampler as defined in claim 1 wherein the aperture through each cap is non-turbulent to thereby prevent the loss of volatile organic compounds.

10. A passive diffusion bag sampler suitable for obtaining concentrations of a variety of volatile organic compounds, said passive diffusion bag sampler comprised of:

an outer protective rigid mesh tube, wherein the rigid mesh tube is cylindrical and sealed at each end;

an inner polyethylene bag that is cylindrical and disposed within the rigid mesh tube, wherein the inner polyethylene bag is sealed at each end and allows the passage of volatile organic compounds to diffuse through a surface of the inner polyethylene bag;

a ring disposed inside each end of the outer protective rigid mesh tube, each ring being rigid and flush with an end of the outer protective rigid mesh tube a cap disposed on each end of the outer protective rigid mesh tube; wherein each cap is inserted inside a corresponding ring to form a tight connection, and wherein the cap is disposed inside the ring but around the outside of a corresponding end of the inner polyethylene bag and is of sufficient length to overlie said end such that insertion of the cap into the ring forms a water-tight seal over the end of the inner polyethylene bag;

an aperture disposed through each cap, wherein the aperture extends from outside the passive diffusion bag sampler to an interior of the inner polyethylene bag; and a plug disposed in the aperture of each cap.

11. A method for obtaining concentrations of a variety of volatile organic compounds using a passive diffusion bag sampler, said method comprising:

providing the passive diffusion bag sampler having an outer protective cylindrical rigid mesh tube that is sealed at each end, an inner polyethylene bag that is cylindrical and disposed within the rigid mesh tube and sealed at each end;

a ring disposed inside each end of the outer protective rigid mesh tube, each ring being rigid and flush with a corresponding end of the outer protective rigid mesh tube, and a cap disposed on each end of the outer protective rigid mesh tube, each cap being inserted inside a corresponding ring to form a tight connection and being disposed inside the ring but around the outside of a corresponding end of the inner polyethylene bag and being of sufficient length to overlie said end such that insertion of the cap into the ring forms a water-tight seal over the end of the inner polyethylene bag;

an aperture disposed through each cap, and a plug in each aperture;

filling the inner polyethylene bag with purified water and sealing the inner polyethylene bag;

disposing the passive diffusion bag sampler in the water sample;

withdrawing the passive diffusion bag sampler after volatile organic compounds have been diffused into the inner polyethylene bag;

cutting one plug from one of the apertures in the passive diffusion bag sampler; and pouring the water from the passive diffusion bag sampler using a first hand.

12. The method as defined in claim 11 wherein the method further comprises providing the aperture wherein the aperture is shaped so as to enable a non-turbulent flow of water from the passive diffusion bag sampler.

13. The method as defined in claim 12 wherein the method further comprises pouring the water from the inner polyethylene bag without the passive diffusion bag sampler bending to a point of folding when it is tipped for pouring.

14. The method as defined in claim 13 wherein the method further comprises:

providing at least one sample vial for storing the water from the passive diffusion bag sampler; and holding the at least one sample vial with a second hand while pouring the water from the passive diffusion bag sampler using the first hand.

15. The method as defined in claim 14 wherein the method further comprises:

providing a first passive diffusion bag sampler as defined in claim 11 having a first attachment loop;

providing a second passive diffusion bag sampler as defined in claim 11 having a second attachment loop; and attaching a coupling link with a safety closure to the first attachment loop and to the second attachment loop such that the first and second diffusion bag samplers are linearly coupled.

16. The method as defined in claim 15 wherein the passive diffusion bag sampler provided in claim 11 includes a ring disposed inside each end of the outer protective rigid mesh tube, each ring being rigid and flush with a corresponding end of the outer protective rigid mesh tube, and wherein each cap is inserted inside a corresponding one of the rings to form a tight connection.

17. A method for obtaining concentrations of a variety of volatile organic compounds using a passive diffusion bag sampler, said method comprising:

providing an outer protective rigid mesh tube, wherein the rigid mesh tube is cylindrical and sealed at each end, an inner polyethylene bag that is cylindrical and disposed within the rigid mesh tube, wherein the inner polyethylene bag is sealed at each end and allows the passage of volatile organic compounds to diffuse through a surface of the inner polyethylene bag, a ring disposed inside each end of the outer protective rigid mesh tube, wherein each ring is rigid and flush with an end of the outer protective rigid mesh tube, and a cap disposed on each end of the outer protective rigid mesh tube to thereby seal the outer protective rigid mesh tube and the inner polyethylene bag, wherein each cap is inserted inside a corresponding ring to form a tight connection and is disposed inside the ring but around the outside of a corresponding end of the inner polyethylene bag and is of sufficient length to overlie said end such that insertion of the cap into the ring forms a water-tight seal over the end of the inner polyethylene bag;

providing an aperture disposed through each cap, wherein the aperture extends from outside the passive diffusion bag sampler to an interior of the inner polyethylene bag, and a non-removable plug disposed in the aperture of each cap;

filling the inner polyethylene bag with purified water and sealing the inner polyethylene bag, disposing the passive diffusion bag sampler at a target location within the water to be sampled;

withdrawing the passive diffusion bag sampler after volatile organic compounds have been diffused into the inner polyethylene bag;

cutting one plug from one of the apertures in the passive diffusion bag sampler; and pouring the water from the passive diffusion bag sampler using a firsthand and in a non-turbulent manner.

18. The method as defined in claim 17 wherein the method further comprises pouring the water from the inner polyethylene bag without the passive diffusion bag sampler bending to a point of folding when it is tipped for pouring.

19. The method as defined in claim 18 wherein the method further comprises:

providing at least one sample vial for storing the water from the passive diffusion bag sampler; and holding the at least one sample vial with a second hand while pouring the water from the passive diffusion bag sampler using the first hand.

20. The method as defined in claim 19 wherein the method further comprises:

providing a first passive diffusion bag sampler as defined in claim 17 having a first attachment loop;

providing a second passive diffusion bag sampler as defined in claim 17 having a second attachment loop;

attaching a coupling link with a safety closure to the first attachment loop and to the second attachment loop such that the first and second diffusion bag samplers are linearly coupled; and providing any number of passive diffusion bags that are attached to a previous diffusion bag using another coupling link with a safety closure.

* * * * *